US005173724A

United States Patent [19]

Bonham et al.

[11] Patent Number: 5,173,724

[45] **Date of Patent: * Dec. 22, 1992**

[54] OPTICAL SYSTEM WHICH HELPS REDUCE EYE STRAIN

[75] Inventors: Celeste V. Bonham, 835 Fernwood Pacific Dr., Topanga, Calif. 90290; Richard D. Rallison, Paradise, Utah

[73] Assignee: Celeste Virginia Bonham, Topanga, Calif.

[ * ] Notice: The portion of the term of this patent subsequent to Aug. 20, 2008 has been disclaimed.

[21] Appl. No.: 626,560

[22] Filed: Dec. 12, 1990

Related U.S. Application Data

[63] Continuation-in-part of Ser. No. 375,834, Feb. 5, 1989, Pat. No. 4,950,067, and a continuation-in-part of Ser. No. 537,110, Jun. 13, 1990, Pat. No. 5,040,888.

[51] Int. Cl.[5] .......... A61B 3/00

[52] U.S. Cl. .......... 351/203; 351/246; 359/1; 359/24

[58] Field of Search .......... 351/201, 203, 206, 246; 359/1, 24

[56] References Cited

U.S. PATENT DOCUMENTS 4,294,522 10/1981 Jacobs .......... 351/203
5,040,888 8/1991 Bonham .......... 351/203

*Primary Examiner*—Bruce Y. Arnold
*Assistant Examiner*—J. P. Ryan

[57] ABSTRACT

An optical system which contains multiple images comprised of two or more images at varying focal distances, which when viewed consecutively and in repetition will exercise the ciliary muscle of the eyes. The optical system may have its own power to illuminate said images. The shifting of conditions of the viewer to alternate the viewing of one image and then the other, may involve the physical movement of the user's head, the system may contain a motor coupled to rotate said system, or the configuration of the lighting source(s) shall illuminate one image and then another. The system may include a clock-timer and control of the variable speed of illumination between one optical image to another. The system may include a sound alarm to remind the viewer to utilize the holographic system.

19 Claims, 2 Drawing Sheets

Fig. 1.
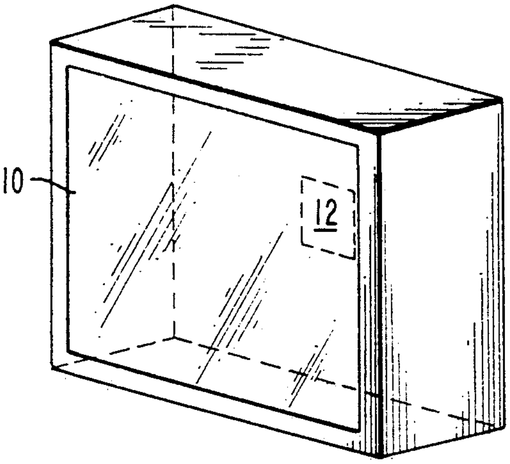
Fig. 2.
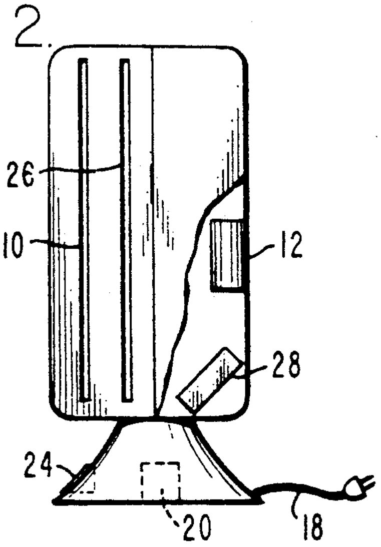
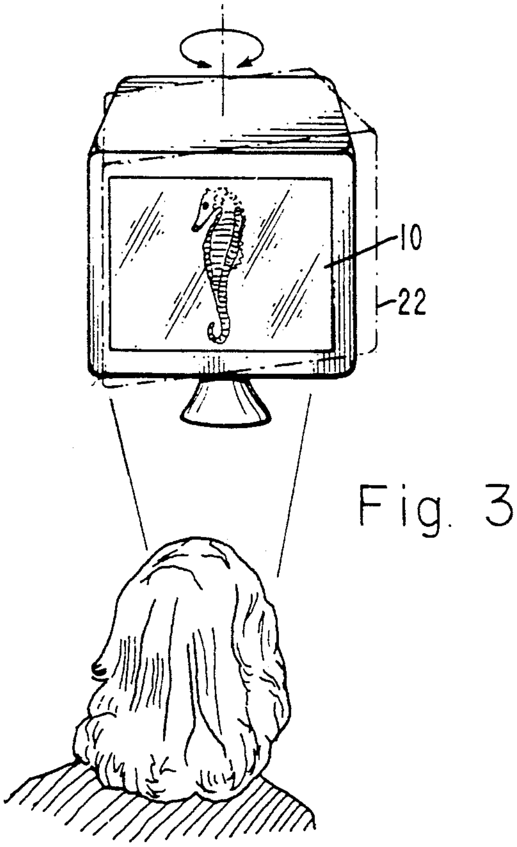
Fig. 3
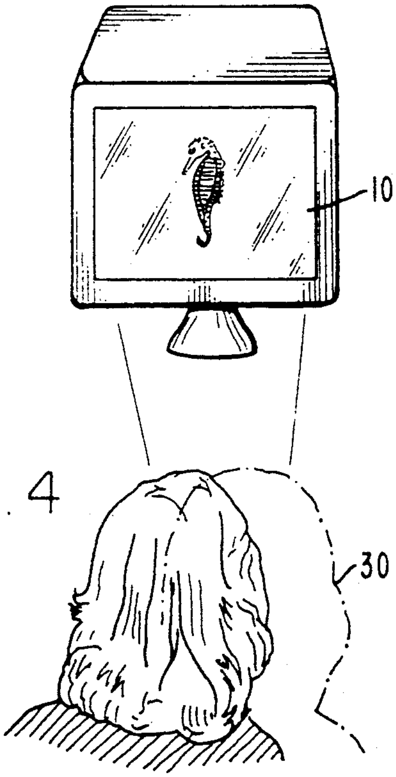
Fig. 4
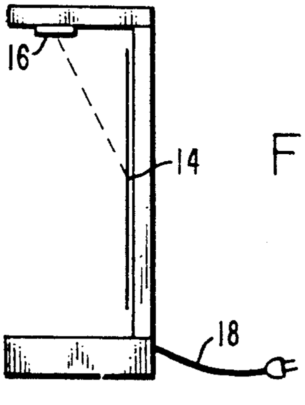
Fig. 5.

OPTICAL SYSTEM WHICH HELPS REDUCE EYE STRAIN

RELATED PATENT APPLICATION

This patent application is a continuation-in-part of Bonham's application Ser. No. 07/375,834, now U.S. Pat. No. 4,950,067, granted Aug. 21, 1990, (HOLOGRAM WHICH HELPS REDUCE EYE STRAIN) as well as her patent pending continuation-in-part (HOLOGRAM SYSTEM WHICH HELPS REDUCE EYE STRAIN) which was filed on Jun. 13, 1990, and is identified by Ser. No. 07/537,110, now U.S. Pat. No. 5,040,888.

BACKGROUND-FIELD OF INVENTION

This invention relates to the exercising of the eye muscles by focusing on optical images successively at varying focal distances. The eye will accommodate when the focusing process relating to these different opticals is accomplished. This exercise will help to reduce eye strain and help to relieve accommodative stress of the eyes when a person does not periodically change focal distances within a given period.

BACKGROUND-DISCUSSION OF PRIOR ART

We live in a computer age where computers are becoming more incorporated into our society with every passing year. Our future will become more computerized as technology broadens and the ease for the user is simplified.

This vast growing industry has lead to a very dangerous medical problem: Weakening of the eyes due to extended viewing of VDTs (video-display terminals). Any work that requires continuous close viewing over long periods of time without exercising and "stretching" the eye muscles can lead to eye strain. This problem is not limited only to the VDT user but can include persons who read extensively, watch television for long periods of time, and anyone whose daily life encompasses extended close viewing over long periods of time. To properly exercise and stretch the ciliary muscle of the eye one must shift focus from distances far to near and back again.

I experienced the difficulty in focusing of vision after extended use on my computer. An eye doctor informed me to take breaks in my work schedule and exercise my eyes. He suggested that I focus on my thumb and then on the corner in the room not closer than a distance of six feet. From an eyesight standpoint, 20 feet is comparable to infinity. Doing this exercise every 15 to 30 minutes for about 10 to 15 seconds would largely reduce the eye strain I was experiencing. I researched in the library editorial section and found a vast array of articles written in such major publications as: U.S. News & World Report, Forbes, Scientific American, PC-Personal Computing, PC Week, etc. Each of these articles noted the growing problem of eye strain in the work place and especially where computers are being used. In May 1989, OSHA released a study on VDT user problems titled, Ad Hoc Expert Advisory Committee On Visual Display Terminals. In this report it states the leading negative effect on the user is the difficulty of focusing after extended use on the VDT. Some articles also stated that the increasingly high percentage of children having to wear glasses at an earlier age than in the past is directly related to eye strain. Research has concluded that children are becoming more indoctrinated and educated on computers aś technology advances. With the growing attraction to television, children are not getting enough eye exercise needed to keep the eyes healthy, thus resulting in early eye impairment and the need of eye glasses. We cannot change man's evolution and the advancement of technology, but with the correct use of this simple invention it can help to avoid the eye impairment caused by improperly using the eyes.

I have not found an invention in the marketplace which directly aids in this problem. Presently, for therapy, eye doctors are using 3-D glasses designed with images to focus upon. The problem with such an eye exercise device as these glasses is that when worn they totally preclude the viewer from seeing anything but that which is photographed inside the glasses. One has to stop all work when wearing these glasses. Searching through the patent library I found no prior art or patents of devices or systems to help strengthen the eye muscles which include and use an optical image which is translucent when not illuminated, such as a holographic image but not limited to such, a lens system, and one or more optical image reproduced through the means of illumination. I searched through U.S. Patent Office Class 350 (Optics Systems & Elements) Subclass 3.7 (Using a hologram as an ordinary optical element) and Subclass 3.84 (Focused image holography); and through Class 351 (Optics—Eye examining, Vision, Testing & Correcting) Subclass 203 (Eye exercising or training type) to no avail. None of the prior art or patents directly utilized a hologram or any type of translucent optical, a lens system, and an optical image that is reproduced through the means of illumination to strengthen the eye muscles by changing focal distances.

With reference to Brown et al. (U.S. Pat. No. 4,376,950) which was brought to my attention by the Patent Examiner, I see no conflict or infringement of patent rights since Brown et al. does not claim to be a device for exercising the eyes. Brown et al. is a patent of successive images wherein my patent deal with an optical system which is comprised of a translucent image, as in a hologram but not limited to such, a lensing system and at least one other illuminated optical image. Brown et al. is a system to reproduce "realities". My system only has one specific and exclusive purpose: to exercise the eye muscles by changing focus length when providing two or more images appearing at different focus distances. My system has the capability of permitting the viewer to first observe one image at a close focal distance, and than observe another image which appears to be distant from the viewer, with only one optical being visible in each case. In one embodiment, my system has the ability to illuminate only one image at a time; thereby darkening the other image(s) when not needed to focus upon the other image.

SUMMARY OF THE INVENTION

In accordance with a broad aspect of the invention, in one imbodiment, the invention may involve a single hologram with multiple images; and in another imbodiment it may be implemented by two successive images, with the foreground image being translucent. In accordance with one illustrative imbodiment of my invention, one image is provided by a translucent optical image, as in a hologram but not limited to such. There shall be two or more images, one image at a near focal distance and one or the others at a farther focal distance. There shall be means of illumination through one or more lighting sources. One image will appear to be close to the viewer and at least one other optical visual, reproduced through the means of illumination, will appear to be at a substantial distance from the viewer at a remote point. A stand mounting may be provided for convenience of the user as well as a means for attachment to a computer casement; and suitable illuminating arrangements provided.

Supplemental features could include a means for directing the light source so that it alternately illuminates one image and then the other, an electrical power circuit and/or battery compartment, a flip-flop or an electronic board which can support circuitry such as an On/Off switch, variable speed control and timing configurations as well as a clock/timer for periodically turning the illumination and/or system on and off, and an alarm system to remind the user to exercise their eye muscles.

The system includes its own light source(s) to illuminate the opticals, thereby giving stronger and more distinctive images to focus upon.

OBJECTS AND ADVANTAGES

Accordingly, there are several objects and advantages to my invention, and certain of these objects are:

a) to provide an exercise for the eye muscles which helps to reduce eye strain;

b) to provide an easily accessible invention for consumers which will help strengthen their eye muscles;

c) to provide an entertaining visual display which will attract the attention of the consumer causing its extended and continued use;

d) to provide an alternative relaxed visual which will also incorporate peace of mind and help reduce stress connected with the extended use of VDTs, books, or television;

e) to provide less stress of the eyes which will reduce headaches and job absenteeism;

f) in addition, opticals will be designed for individual age groups, thereby attracting its use to a broader age range from young children to adults.

Further advantages will become apparent from a consideration of the following description and the accompanying drawings.

BRIEF DESCRIPTION OF DRAWINGS

FIG. 1 is a perspective view of a holographic system illustrating the invention when a transmission hologram is used;

FIG. 2 is the side view of my invention showing the hologram, the light system, a backing board, a clock and/or timer, an electrical source, mirror(s) to reflect light, and a motor which could cause the box itself to move the appropriate distance to change the holographic images in my invention for the viewer;

FIG. 3 and FIG. 4 are perspective views each illustrating an embodiment of my invention when used by a viewer. These FIGS. 3 and 4 illustrate the image changing in the hologram with a slight movement of the head, or the movement of the light box itself, respectively; and FIG. 5 is a side view of the holographic system wherein a reflective hologram is used; thereby requiring a light source to illuminate the hologram from a frontal position.

FIG. 6 also shows the invention as it sits upon the top casement of a computer.

DETAILED DESCRIPTION OF PREFERRED EMBODIMENTS

Figure 6:
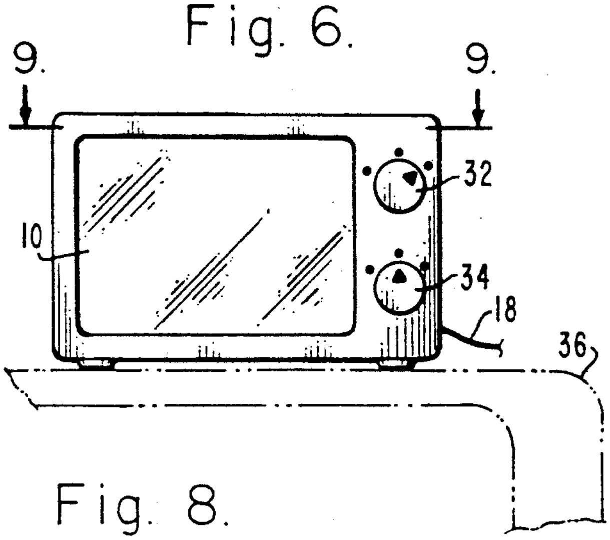
FIG. 6 is another embodiment of the invention showing the display and controls for variable speeds and timer.

There are more than one illustrative embodiments of my invention. One embodiment uses a multiplex holographic optical system and in another there is a translucent image and at least one other distant image to focus upon. In the latter stated embodiment, the translucent image, which may be the close image, should not impair the viewer's sight when viewing the other (distant) image(s). A hologram is an example of a translucent image. When the hologram is not illuminated it appears to be only a thin plate of glass or plastic and will not obstruct the viewer's focusing on the other image(s).

A hologram is a medium which enables the storage of three-dimensional visual information on a two-dimensional plane. A hologram is not a new invention. It was first invented in 1947 by Dr. Dennis Gabor and has been successfully improved over the years.

In one embodiment of the invention you might need to use an image multiplex hologram. The image multiplexing opticals within the hologram will be recorded with a laser light on an unexposed emulsion (glass or film) while facing a three-dimensional object. The Image Multiplexing chapter in the book, HOLOGRAPHY, Expanded and Revised from the French Edition, by M. Francon, fully details and explains the image multiplexing process for holography. The laser, emitting a beam of pure coherent light, is optically split into two beams on a complex optical vibration isolation table. One beam is used to illuminate the real three-dimensional object which reflects its light properties onto the emulsion, while the other beam is directed straight at the emulsion. The film receives the patterns of both the object's reflected light (the object beam) and the direct laser light (the reference beam) resulting in an interference pattern recording where the beams intersect on the unexposed emulsion.

To acquire the image multiplexing within the hologram, the signal (object) to be recorded is placed adjacent to a diffuser which is illuminated by a laser. Between the signal and the photographic plate is a diaphragm with an aperture which will be formed from more than one sector. The plate is illuminated by a reference beam to record a hologram as previously described in preceeding paragraph. After the first exposure, the signal is replaced by a different signal and a second exposure is made with the sectors rotated to occupy another position or "window" on the plate which does not overlap the first. By using an actual diaphragm to isolate one of the images in a given window, we reconstruct only that signal to which it corresponds. Several exposures are made each having their own window with the signal to be recorded and the position of the sectors changed each time. The film is then developed recording the information of the object and its light patterns. After development, the hologram is placed precisely in its initial position and each window is illuminated by a reference wave. The hologram is illuminated either with a laser or incandescent light source positioned at the exact angle of the original reference beam recording. The interference pattern is then activated, causing the recording of the original object in each window to appear in the hologram exactly as it originally was, suspended in space, in all its total dimension. In my one embodiment of my invention a holographic system will be used to display two or more three-dimensional opticals at various focal distances contained in the single hologram. Each recording will be illuminated by positioning the light source at the exact angle of the original reference beam recording. To change the position of the reference beam onto another window of the hologram and illuminate the object, a slight movement of the head or the movement of the system itself will cause the images in the hologram to change. There can also be integrated a switching means so that the light is moved from one image to the other.

The size of the hologram will vary depending on the dimensions of the hologram support and illumination. There is no limitation to the size or the shape (square, circle, rectangular, etc.) of the hologram. The hologram can be displayed in a free standing, self-contained display, and may include its own light source, clock, timer, or motorized device which will move or rotate the display box by the appropriate distance or angle to change the images viewed in the hologram.

This embodiment of the invention can be either a transmission hologram (FIG. 1) or a reflective hologram (FIG. 5). The difference of these are determined by the placement of the light source configuration and the type of hologram which is used. In a transmission hologram (FIG. 1) the viewing light source 12 will apply illumination through the hologram 10, which is between the viewer and the light source 12. For a reflective hologram (FIG. 5), the hologram 14 will be illuminated by the reflection of an exterior light 16 positioned at the appropriate angle in front of the hologram 14. In both the transmission and reflective holograms the light source 12,16 will be powered by means of an electrical source 18 or batteries. The side illustration (FIG. 2.) of a transmission system shows the hologram 10, and the motor 20 which can cause the display box to pivot to the position indicated at reference numeral 22 as shown in FIG. 3. FIG. 2. also shows the light source 12, electrical power source 18, clock/timer 24 which can be programmed to periodically activate the light source 12 and the motor 20, a backing board 26 behind the hologram to block extraneous objects from the viewed holographic images, and a mirror 28 to reflect the light thus allowing the light from the light source 12 to travel to the holographic image 10, in a manner known in the holographic field.

FIG. 3 and FIG. 4 demonstrate two practical uses of the system. FIG. 3 demonstrates the holographic image 10 changing due to the slight movement of the system 22, as the hologram 10 is rotated by motor 20. FIG. 4 demonstrates the holographic image 10 changing by the slight movement of the head as indicated by reference numeral 30. In FIGS. 3 and 4, examples are given showing a seahorse image which appears to be close to the viewer in FIG. 3, and one which appears to be remote from the viewer in FIG. 4. In practice, the two or more images would be contained in one hologram, and would be changed by relative movement of the hologram and the viewer, either as shown in FIG. 3 or in FIG. 4.

Figure 7:
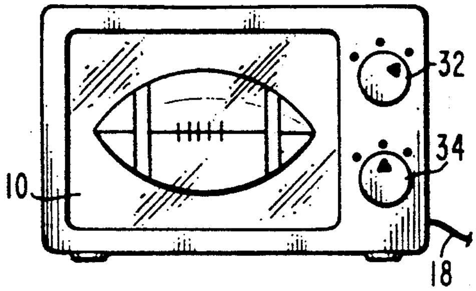
FIG. 7 shows the embodiment of the invention shown in FIG. 6 when the near translucent image is illuminated.
Figure 8:
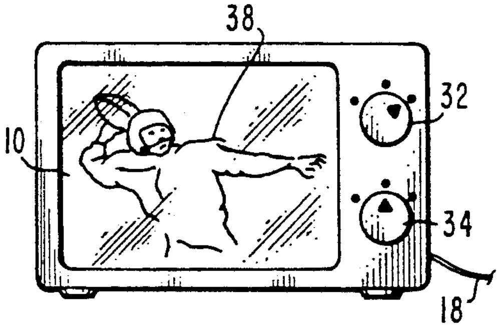
FIG. 8 shows the embodiment of the invention shown in FIG. 6 when the far image is viewed when illuminated.
Figure 9:
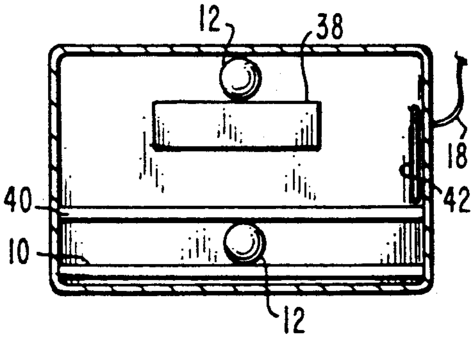
FIG. 9 is the embodiment of the invention shown in FIG. 6 from a cutaway overhead view showing the translucent image, lensing system, second image, lighting system, and an electronic circuit board which may include flip-flops and other circuitry.
Figure 10:
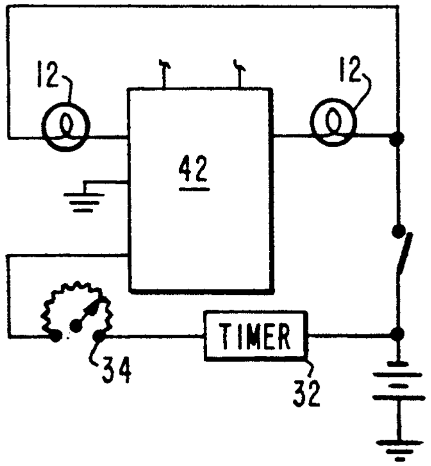
FIG. 10 shows the circuit system provided by a flip-flop, electronic device which has circuitry to the lighting system(s), on and off, timer, variable speed, and grounds.

Another embodiment of my invention is shown in FIGS. 6 through 10. FIG. 6 shows the casement which includes a timing control 32 and a variable speed control 34. FIG. 6 also displays the invention on the top casement of a computer unit 36. FIG. 6 shows the invention when there is no illumination on any of the opticals housed within the unit. In FIG. 7 the invention is shown when the close image 10, the translucent image, is illuminated. In FIG. 8 the invention is shown when the distant image 38 is illuminated. FIG. 8 also shows that when the close image 10 is not illuminated there is no obstruction for the viewer to focus on the distant image(s). FIG. 9 shows the overhead view of the invention displaying the configuration of elements contained within the invention. This configuration shows two lighting sources 12 but the invention can be designed with only one lighting source which could be controlled by a mirror. The translucent image 10 is illuminated by a lighting source 12. Between the first image 10 and the second image 38 there is a lensing system 40 comprised of a "positive magnifying lens". The distance between the lens and the distant image(s) is not vital to the proper working on my invention. The second image 38 also may be designed to have its own light source 12. There is electronic circuitry including a circuit board bearing a flip-flop 42 and other circuitry of generally conventional type for the varying speeds and controls. FIG. 10 shows a circuit board where the wiring is connecting a flip-flop to the lighting source(s) 12, timer 32, variable speed control 34 as well as ground connections.

My invention is not limited to only one embodiment. I have detailed more than one in my description and drawings. My invention can have a wide array of optical visuals—the images are limitless with the only prerequisite that there is a change of focal distances within the two or more opticals contained within the systems implementing my invention.

OPERATION OF INVENTION

The manner of using the first embodiment FIG. 1 when a hologram system is used is quite simple. First of all, the light source 12 is activated to illuminate the opticals contained in the film of the hologram 10. The light source 12 can be illuminated at all times or can be controlled by a switch, button, voice activation or preprogrammed with a timer and/or clock 24. Focus on one of the images in the hologram. Once you have a strong focus on this image displayed in the hologram, slightly move your body 30 to change the position of your head and eyes FIG. 4, or if the box is motorized 20 it will automatically change the position of the box 22 in FIG. 3., and another image at a different focal point will be visible. Focus on this new image in the hologram. Once you have a strong focus of this image, slightly change the position of your head and eyes 30, or the box will automatically return to the first position 22, and you will return to your first image. If the hologram is designed with more than two images, then with the different positions of the body and the box each image within the hologram will have its position of visibility. The images will be designed to give the viewer images with various focal points. The viewer shall also be able to change the images if he/she so chooses.

To properly exercise the ciliary muscles, focus on these images for not less than ten to fifteen seconds every fifteen to thirty minutes and this will exercise your ciliary eye muscles thus helping to reduce eye strain. The clock/timer 24 is provided with an alarm which may be selectively turned on to alert the user to view the system of the present invention at intervals as noted above.

In another embodiment as shown in FIGS. 6 through 10, the invention is easily used. First of all activate the power source 18 which may be a battery or house current. Choose the time setting by the turn of the timing knob 32 and the setting of the variable speed control 32 which switches from illumination of one image to the illumination of another at a different apparent focal length. A recommended variable speed could include 1.5 sec., 3.0 sec., and 5.0 sec. An alarm can be included in the system which will alert the user at predetermined time intervals (such as 15 minutes) that the visuals are being illuminated. The invention will be "off" until the timer is set and activates the illumination of the lighting system 12, and there is an override position on the timer whereby the users can use the system at their own discretion. Focus on one of the images in the optical system. Depending on the variable speed control you have chosen, the image will change to another optical image at a different focal distance. This shall be continued until the automatic timer has turned the system "off". FIG. 6 shows the invention placed on the top of a computer casement 36. This will be very practical and handy for any VDT user and shall not take up any needed desk space. If the user is using the timer 32 then once the completed timed cycle is finished the unit will automatically go "off" again and not be illuminated, that is until the timed cycle renews itself. If the user is using the timer 32 then the user must manually turn off the invention; otherwise the cycle of time will continue.

The user has the option of changing the optical images.

CONCLUSION AND RAMIFICATIONS

Thus the reader will see that this invention provides a very simple solution to a vast growing problem of eye strain by exercising the ciliary eye muscles. This problem has been greatly acknowledged and emphasized within the computer age we live in. The simplicity of the invention allows for this to be a very reasonable and economical device. Furthermore, it has the additional advantages in that:

- it is not limited to one age group but allows children as well as adults to benefit from its use;
- it is economically accessible to the consumer;
- with entertaining, interesting, and relaxing optics, the viewer will be more apt to want to use the invention, whereby the more one uses the invention, the more the ciliary muscle is exercised.

While my above description contains specifications, these should not be construed as limitations on the scope of the invention, but rather as an exemplification of preferred embodiments thereof. Many other variations are possible. For example: FIG. 1 and FIG. 5 shows existing types of display units when the invention utilizes the technology of holography. FIG. 6 shows the invention displayed on the top casement of a computer. FIG. 7 and FIG. 8 show the invention when any translucent image is used in conjunction with a lensing system and at least one more optical image. Ultimately, I see this invention being incorporated within a software program so that with a touch of a finger the optical images will appear on the screen of the VDT monitor whereby the user may have easy access to the use of the invention.

Accordingly, the scope of the invention should be determined not by the embodiment illustrated, but by the appended claims and their legal equivalents.

I claim:

1. A method of stimulating the eye muscles with an optical system having multiple images in a single field of view appearing to be located at significantly different distances from the viewer, one image appearing to be very close to the viewer and at least one other image substantially at an infinite distance from the viewer, comprising the steps at:

(a) mounting the optical system in a light box casement housing;

(b) illuminating the optical images;

(c) having a viewer strongly focus on one of the optical images appearing to be at one distance from the viewer;

(d) shifting the optical conditions to present to the viewer another image appearing to be at a different distance from the viewer and having the viewer strongly focus on this different image, thereby exercising the viewer's eye muscles; and (e) said steps including viewing one of said images through a magnifying lens.

2. A method as defined in claim 1 wherein the shifting of the conditions involves the movement of the light box casement housing the invention.

3. A method as defined in claim 1 wherein said system includes a first foreground translucent image and a second image spaced back from said foreground image, and including the additional step of alternating illumination of said first and second images.

4. A method as defined in claim 3 wherein the alternating illumination of the optical images includes the use of a variable speed control.

5. A method as defined in claim 1 wherein the activating of the illumination of the optical images involves the use of a clock/timer.

6. A method as defined in claim 5 wherein the clock/timer periodically sounds an alarm to alert the viewer to use the invention.

7. A method of performing tasks involving continuous close viewing and periodically interrupting such tasks and performing steps (a) through (d) set forth hereinabove stated in claim 1.

8. A method as defined in claim 1 wherein the step of shifting the optical conditions is controlled by an electronic circuit board or a flip-flop.

9. A method as defined in claim 1 for use by persons operating video display terminals, comprising the additional step of operating a video display terminal for periodic intervals, and then interrupting the operation of the video display terminal and performing the steps of claim 1 for an interval of time before resuming operation of the terminal.

10. A system for stimulating and exercising the eye muscles comprising:

an optical system including means for viewing multiple images in a single field of view appearing to be located at significantly different distances from the viewer, one very close to the viewer and one at an infinite distance from the viewer, said means including a hologram;

means for mounting said optical system on a stand;

means for illuminating said optical system;

means for permitting shifting conditions for the user to alternate viewing one image and then the other; and means including a magnifying lens for enhancing the viewing of one of said images.

11. A system as defined in claim 10 wherein said system includes a first foreground translucent image and a second image spaced back from said foreground image, and including the additional step of alternating illumination of said first and second images.

12. A system as defined in claim 11 wherein the alternating illumination of the optical images includes a variable speed control.

13. A system as defined in claim 10 for including a timer/clock to activate said illumination means.

14. A system as defined in claim 10 wherein a timer/-clock is provided to periodically sound an alarm to alert the viewer to use the invention.

15. A system for stimulating and exercising the eye muscles comprising:

two or more optical images in a single field of view appearing to be located at different distances from the viewer, a translucent optical image appearing to be located close to the viewer, one or more optical images appearing to be at an infinite distance from the viewer;

means for housing said optical system in a light box casement;

means for illuminating said optical system; and means for permitting shifting conditions for the user to alternate viewing one image and then the other.

16. A system as defined in claim 15 wherein said system includes a positive magnifying lensing system.

17. A system as defined in claim 15 wherein said system includes a variable speed control for alternating the illumination of the optical images.

18. A system as defined in claim 15 wherein said system includes timer means for periodically activating the system.

19. A system as defined in claim 15 wherein said system includes a sound alarm actived by clock/timer to remind the viewer to utilize the display.

* * * * *